United States Patent
Yang et al.

(10) Patent No.: US 7,750,790 B2
(45) Date of Patent: Jul. 6, 2010

(54) FABRIC-BASED STRAIN GAUGE

(75) Inventors: Chang Ming Yang, Jhunan (TW);
Chun-Mei Chou, Jhunan (TW)

(73) Assignee: Chang-Ming Yang, Miaoli (TW)

( * ) Notice: Subject to any disclaimer, the term of this patent is extended or adjusted under 35 U.S.C. 154(b) by 839 days.

(21) Appl. No.: 11/655,199

(22) Filed: Jan. 19, 2007

(65) Prior Publication Data

US 2007/0171024 A1    Jul. 26, 2007

(30) Foreign Application Priority Data

Jan. 23, 2006   (TW) ............................... 95102508 A

(51) Int. Cl.
*G01L 1/22* (2006.01)
(52) U.S. Cl. .............................. 338/2; 338/99; 338/114; 428/357; 428/364; 442/2
(58) Field of Classification Search .................... 338/2, 338/99, 101, 114, 210, 212, 259; 442/229, 442/256, 2; 428/357, 364, 408; 73/760, 73/768
See application file for complete search history.

(56) References Cited

U.S. PATENT DOCUMENTS

| | | | | |
|---|---|---|---|---|
| 4,515,866 A | * | 5/1985 | Okamoto et al. | 428/614 |
| 4,659,873 A | * | 4/1987 | Gibson et al. | 178/18.05 |
| 6,277,771 B1 | * | 8/2001 | Nishimura et al. | 442/229 |

\* cited by examiner

*Primary Examiner*—Kyung Lee
(74) *Attorney, Agent, or Firm*—Osha • Liang LLP

(57) ABSTRACT

The invention provides a strain gauge which includes a fabric base and at least one conductive yarn. In addition, the fabric base is weaved with a plurality of non-conductive yarns, and the fabric base thereon defines a sensing direction. Moreover, each of the conductive yarn is gimped by a textile process with one of the non-conductive yarns and is woven through the fabric base along the sensing direction. Furthermore, the at least one conductive yarn is capable of being applied by an electric power; when an external force acts on the fabric base, the geometrical property of the at least one conductive yarn alters so that a change of an electric property associated with the applied electric power is sensed to indicate an elongation of said strain gauge applied by the external force along the sensing direction.

14 Claims, 6 Drawing Sheets

FABRIC-BASED STRAIN GAUGE

BACKGROUND OF THE INVENTION

1. Field of the Invention

The invention is related to a strain gauge and, more particularly, to a fabric-based strain gauge.

2. Description of the Prior Art

Strain gauge, or named strainometer, of the prior art used to be a metal wire formed by a resistor with a constant resistance, such as 120 ohm, 350 ohm, or 1000 ohm. Furthermore, based on the principle that the proportion of the change of the length of the metal wire and the change of resistance of the metal wire is directly proportional, when an external force, such as a pulling force, pressure, tension, and other forces, acts on the metal wire and causes change in the length of the metal wire, the change of its resistance and the change of its length are directly proportional. Therefore, we can calculate the strength of the external force by measuring the change of its resistance.

Because of the simple principle and convenient usage, strain gauge has been widely applied in the prior art for the measurement of many physical vectors, such as the strain gauge element disclosed in U.S. Pat. No. 5,199,519; the strain gage disclosed in U.S. Pat. No. 4,920,806; the force measuring apparatus that contains a strain gauge disclosed in TW Pat. App. No. 094200558; and the torque wrench with a plurality of strain gauges disclosed in TW Pat. App. No. 094205393.

Generally, strain gauge is mounted to a solid structure, such as buildings, machines, tools, in a Wheatstone Bridge form to measure the strength of force received by the solid structure or its deformation. Because the strain gauge as described above is usually mounted to the solid structure through adhesion, it is hard to be mounted on a living body, such as human body or limbs of animals, to measure the movement of the living body.

In another aspect, with the gradual change in age structure, more and more old people need medical care, and a variety of physical function monitoring apparatus have became the focus of the medical equipment industry. Recently, a lot of such apparatus/systems have been developed to monitor physical functions, such as respiration, heartbeat, body motion, etc. For example, the wireless medical monitoring method and system is disclosed in TW Pat. No. 125438; the physical function monitoring apparatus combined with mobile phone is disclosed in TW Pat. No. 179015; and the apparatus and method for monitoring physical function is disclosed in TW Pat. App. No. 091110321.

However, most of the physical function monitoring apparatus/systems as disclosed in the references above have to perform monitoring at a fixed location, thus reducing mobility, and it may fail to perform monitoring because of user's carelessness. Additionally, some of the monitoring apparatus as described above can be worn on a user, so as to perform monitoring at anytime and anywhere; however, the weight and size of these apparatus may be a burden or may cause difficulty in the movements of the user.

In summary, there is a need for wearable physical function monitoring apparatus and further for comfortably wearable physical function monitoring apparatus, especially combining with the use of the strain gauge.

SUMMARY OF THE INVENTION

The objective of the present invention will no doubt become obvious to those of ordinary skill in the art after reading the following detailed description of the preferred embodiment, which is illustrated in the various figures and drawings.

Therefore, an aspect of the invention is to provide a strain gauge, and more particularly, the strain gauge of the invention is based on a fabric, and therefore, has excellent flexibility, it can be integrated with a variety of fabrics to be worn on any objects.

The strain gauge according to a preferred embodiment of the invention includes a fabric base and at least one conductive yarn.

The fabric base is weaved with a plurality of non-conductive yarns, and the fabric base thereon defines a sensing direction.

Moreover, each of the conductive yarn is gimped with one of the non-conductive yarns by a textile process and is woven through the fabric base along the sensing direction.

In addition, the at least one conductive yarn is capable of being applied by an electric power. When an external force acts on the fabric base, the geometrical property of the at least one conductive yarn is altered, so that a change of an electric property associated with the applied electric power can be sensed to indicate an elongation of said strain gauge applied by the external force along the sensing direction.

The scope of the present invention will no doubt become obvious to those of ordinary skill in the art after reading the following detailed description of the preferred embodiment, which is illustrated in the various figures and drawings.

BRIEF DESCRIPTION OF THE APPENDED DRAWINGS

DETAILED DESCRIPTION OF THE INVENTION

As used herein, the term "fiber" refers to staple fiber (short fiber) or filament (long fiber).

According to a preferred embodiment of the invention, the strain gauge includes a fabric base and at least one conductive yarn.

The fabric base is weaved with a plurality of non-conductive yarns, and the fabric base thereon defines a sensing direction. In an embodiment, the plurality of non-conductive yarns have elasticity, so that the strain gauge can fit to any kind of surface, such as chest, elbow, and knee, to enhance the sensitivity and accuracy of measurement. For example, the non-conductive yarns can be natural elastic yarns, or synthetic elastic yarns. However, in another embodiment, parts of the plurality of non-conductive yarns can optionally have different elasticity. In yet another embodiment, only one or several of the plurality of non-conductive yarns have elasticity.

Furthermore, each of the conductive yarn is gimped with one of the non-conductive yarns by a textile process and is woven through the fabric base along the sensing direction, such as a horizontal direction or a vertical direction.

Additionally, the at least one conductive yarn is capable of being applied by an electric power. When an external force acts on the fabric base, the geometrical property, e.g. elongation or width, of the at least one conductive yarn is altered, so that a change of an electric property, e.g. impedance or magnetic flux or electric flux, associated with the applied electric power can be sensed to indicate an elongation or contraction of said strain gauge applied by the external force along the sensing direction.

Figure 1A:
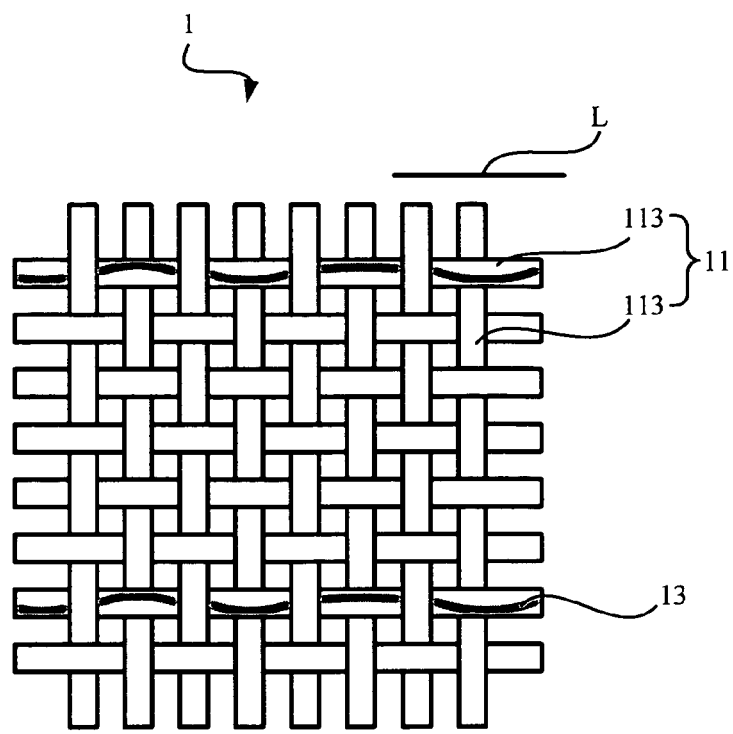
FIG. 1A shows the structure of a strain gauge of the invention, and each of the at least one conductive yarn is gimped with one of the non-conductive yarns by a weaving process.

Please refer to FIG. 1A; in an embodiment as mentioned above, the strain gauge 1 includes a fabric base 11 and at least one conductive yarn 13. Moreover, the fabric base 11 therein defines a sensing direction L. Particularly, in the embodiment, each of the at least one conductive yarn 13 is gimped with one of the non-conductive yarns 113 along the sensing direction L by a weaving process.

Figure 1B:
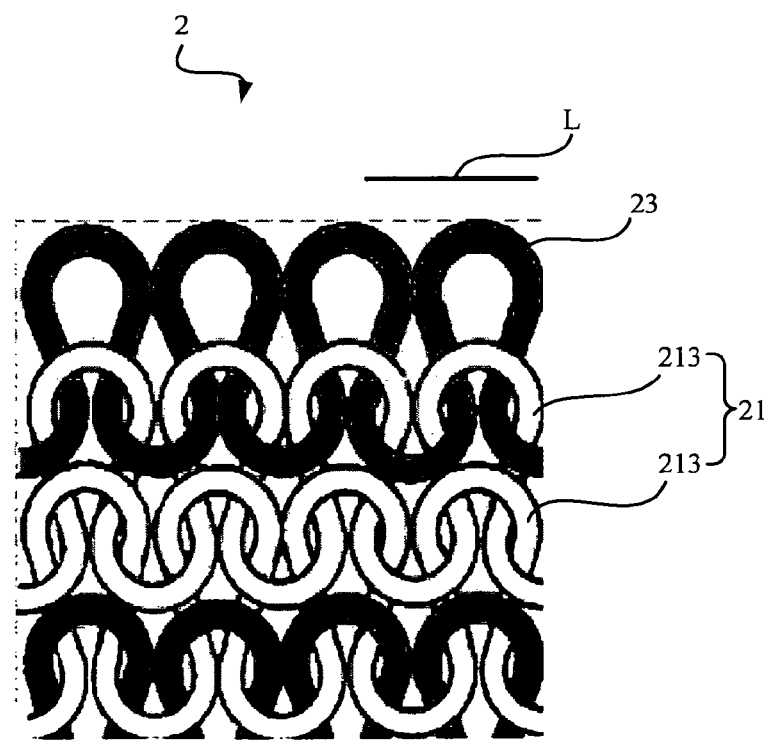
FIG. 1B shows the structure of a strain gauge of the invention, and each of the at least one conductive yarn is gimped with one of the non-conductive yarns by a knitting process.

Additionally, please refer to FIG. 1B; in another embodiment, each of the at least one conductive yarns 23 is gimped with one of the non-conductive yarns 213 along the sensing direction L by a knitting process.

Figure 2:
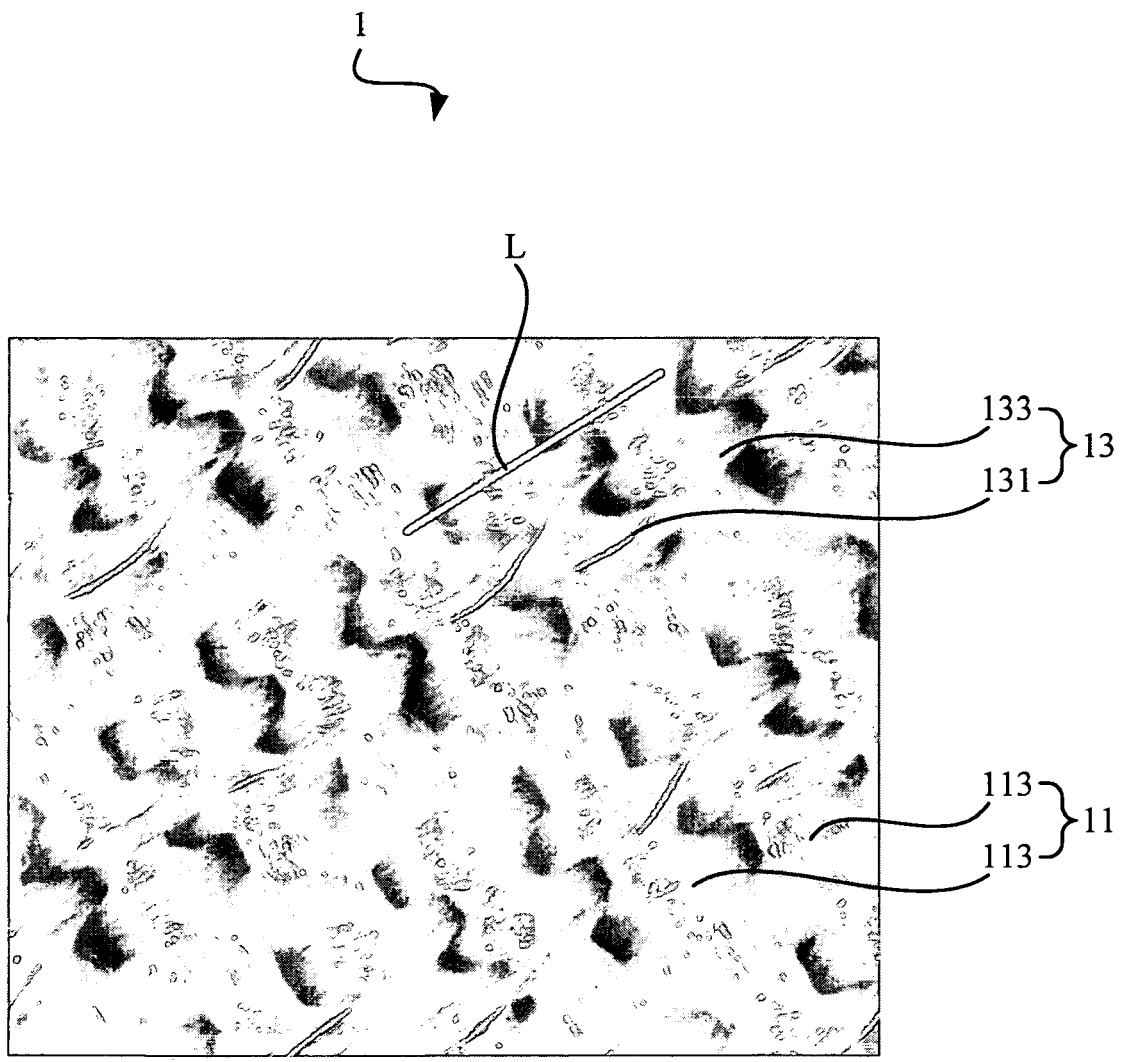
FIG. 2 is a three dimensional microscopic image of a strain gauge of an embodiment of the invention.

Please further refer to FIG. 2, which is a three dimensional microscopic image of a strain gauge of an embodiment of the invention. As described above, the strain gauge 1 includes a fabric base 11 and at least a conductive yarn 13. Additionally, the fabric base 11 is weaved from a plurality of non-conductive yarns 213, and the fabric base 11 thereon defines a sensing direction L.

Particularly, the structure of the strain gauge 1 is that each of the at least one conductive yarn 13 is gimped with one of the non-conductive yarns 113 by a weaving process, as shown in FIG. 1A, and is woven through the fabric base 11 along the sensing direction L.

Also referring to FIG. 2, each of the at least one conductive yarn 13 is formed from an ultra-fine metal wire 131 twisted with a plurality of textile fibers 133.

Practically, each of the ultra-fine metal wire 131, as mentioned above, can be made from stainless steel, a Ni—Cr alloy, or a Cu—Cr alloy. Furthermore, the diameter of each of the ultra-fine metal wire is in between 10 μm and 80 μm.

Moreover, in practice, the plurality of textile fibers 133 can be selected based on the environment applied, and it generally is natural fibers or synthetic fibers, such as cotton fibers, PET fibers, Aramid fibers, and any other textile fibers.

Furthermore, according to the prior arts, the density and distribution of the conductive yarns on the fabric base can be changed to fit different application requirements. In another aspect, because the strain gauge of the embodiment described above applies ultra-fine wire as the material of the conductive yarns, it is more durable and difficult to break, and it further can prevent lost of efficacy or contamination caused by breakage.

Figure 3:
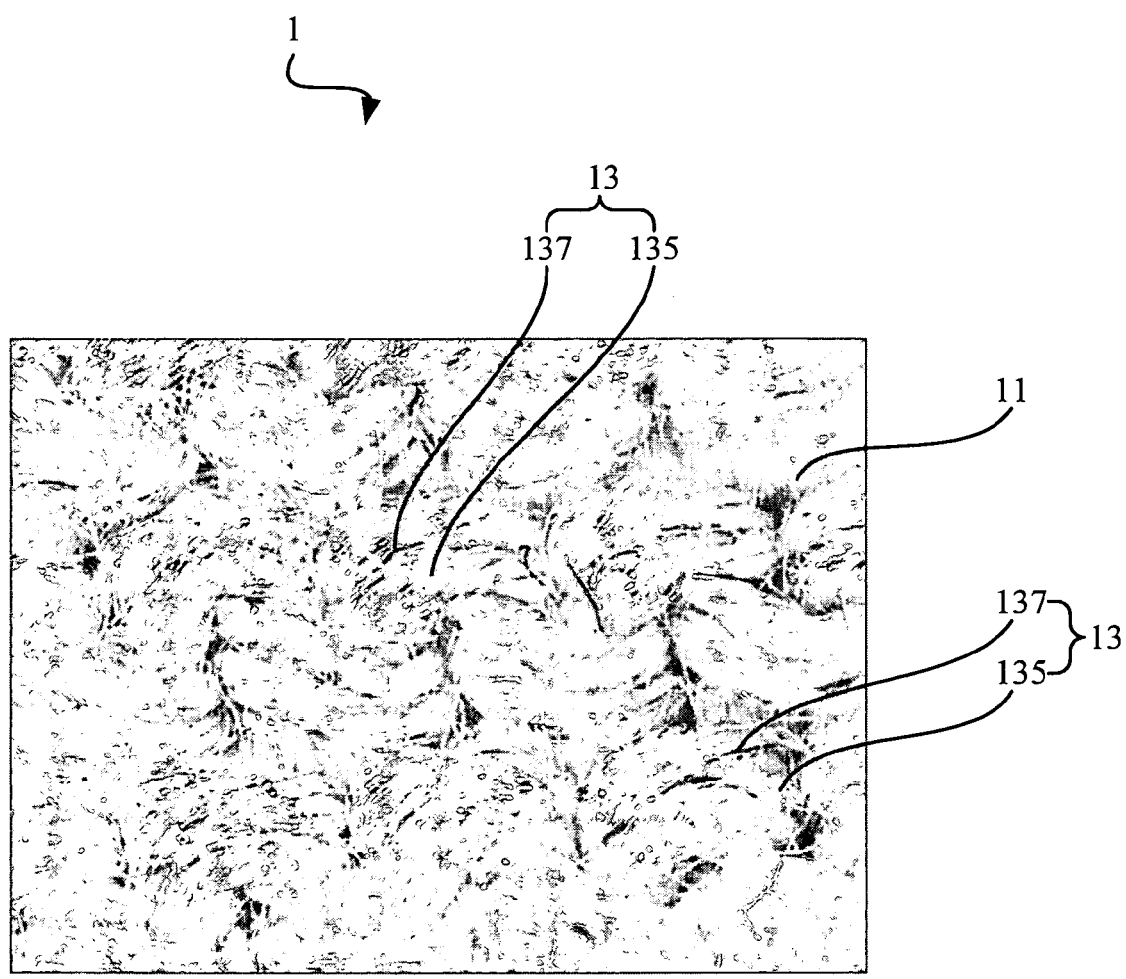
FIG. 3 is a three dimensional microscopic image of a strain gauge of an embodiment of the invention.

Please further refer to FIG. 3, which is a three dimensional microscopic image of a strain gauge of another embodiment of the invention. In the embodiment, the strain gauge 1 also includes a fabric base 11 and at least a conductive yarn 13. Additionally, each of the at least one conductive yarn 13 is substantially formed from textile fibers 135 and metal fibers 137, and each of the at least one conductive yarn 13 contains the metal fibers 137 in an amount between 1 to 100 volume percentage.

Practically, the metal fibers 137 can be stainless steel fibers, Ni—Cr alloy fibers, or Cu—Cr alloy fibers. Moreover, the diameter of each of the metal fibers 137 mentioned above is in between 1 μm and 30 μm.

In another embodiment, each of the at least one conductive yarn is substantially formed from textile fibers and metallic fibers, and each of the at least one conductive yarn contains the metallic fibers in an amount between 1 to 100 volume percentage.

Practically, the metallic fibers can be formed of natural fibers, synthetic fibers, carbon fibers, or glass fibers, coated with Cu, Al, or Ag.

In practice, the strain gauge of the invention can be combined with a variety of fabrics, such as garment, elbow support, knee support, pillow, and mattress, by textile technologies well-known in the prior art, such as piece together, seaming, pasting, and hooking, so as to be applied for measurements in different fields.

For example, when the strain gauge is combined with a pillow, it can be used to monitor the sleeping condition of a user. When the user moves or turns his/her head, the received force of strain gauges in different regions of the pillow will be changed, and that causes the change of electric property of these strain gauges. Therefore, the mode and frequency of the user to move or turn his/her head can be concluded by recording and analyzing the change of electric property of these strain gauges, as a reference for improving sleep quality.

For instance, when the strain gauge is combined with an elbow support, it can be applied to monitor the movement of the user's, like an athlete, elbow. When the user wears the elbow support and move his/her arms, such as to bat, to hit with a racket, or to shoot a basketball, the change in frequency of the electric property of the strain gauge(s) can reflect the frequency of the user's movement, whereas the intensity of the electric property of the strain gauge(s) can reflect the strength and speed of the user's movement.

Figure 4:
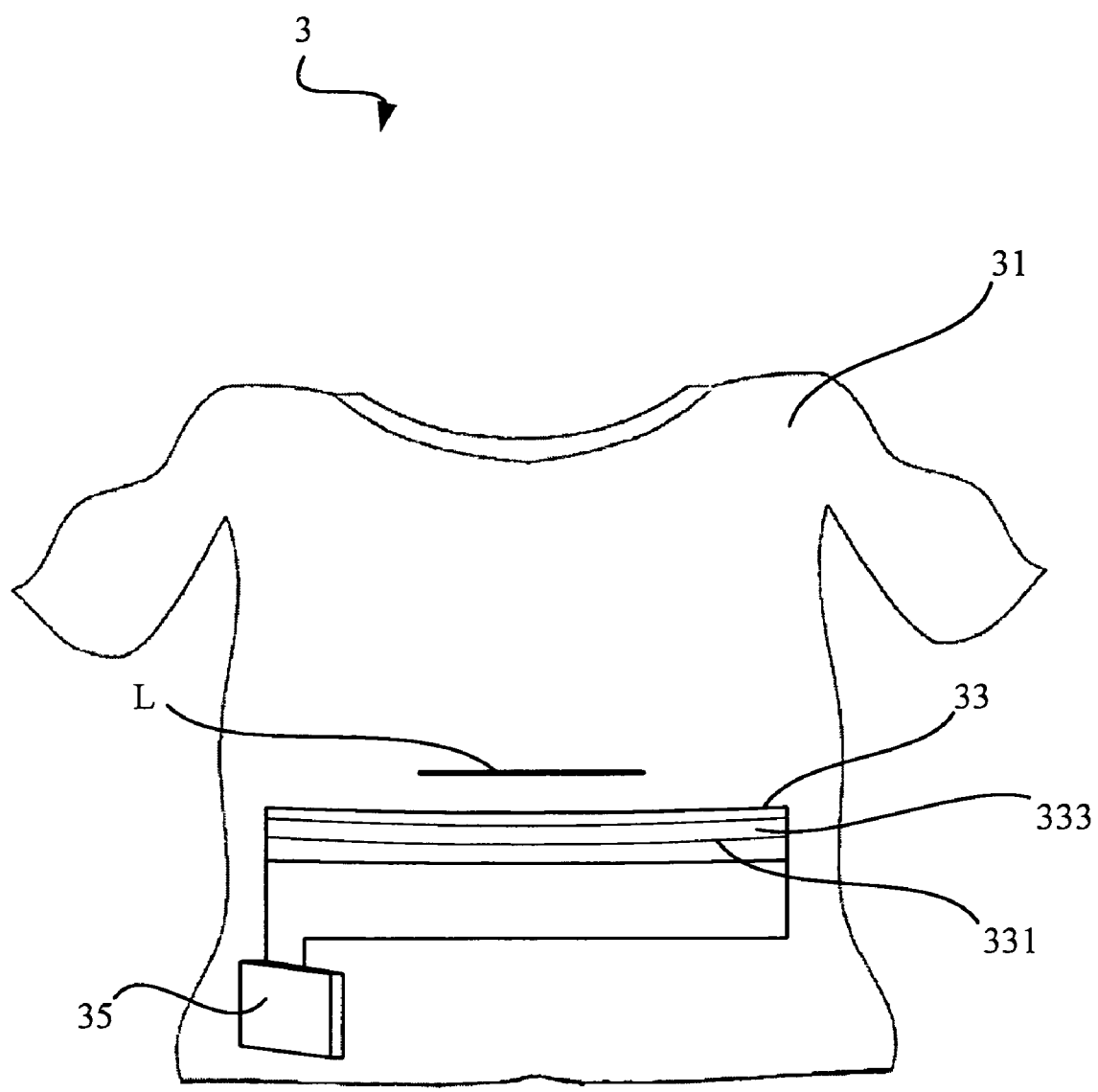
FIG. 4 is a schematic diagram of a practical application of the invention.

Referring to FIG. 4, it is a schematic diagram of a practice of the invention. In the practical application, a physical monitoring system 3 is disclosed, and the physical monitoring system 3 includes a garment 31, a strain gauge 33 of the invention, and a monitoring module 35. In practice, the garment 31 can be worn by a user, so that the strain gauge 33 is located at the abdominal region or chest of the user to monitor respiration of the user. Particularly, the strain gauge 33 has a sensing direction L, and the conductive yarns 331 in the strain gauge 33 is woven through the fabric base 333 of the strain gauge 33 along the sensing direction L by a weaving process.

Furthermore, the strain gauge 33 is electrically connected to the monitoring module 35. The monitoring module 35 can further include a power supplying device, a recording device, a processing device, and a display device. The power supplying device, such as a battery, is used to supply an electric power to the conductive yarns 331; the recording device is used to record the change of an electric property of the conductive yarns 331 when the user respires, and the processing device is used to process the signal recorded by the recording device and to display the processed signal via the display device.

Figure 5:
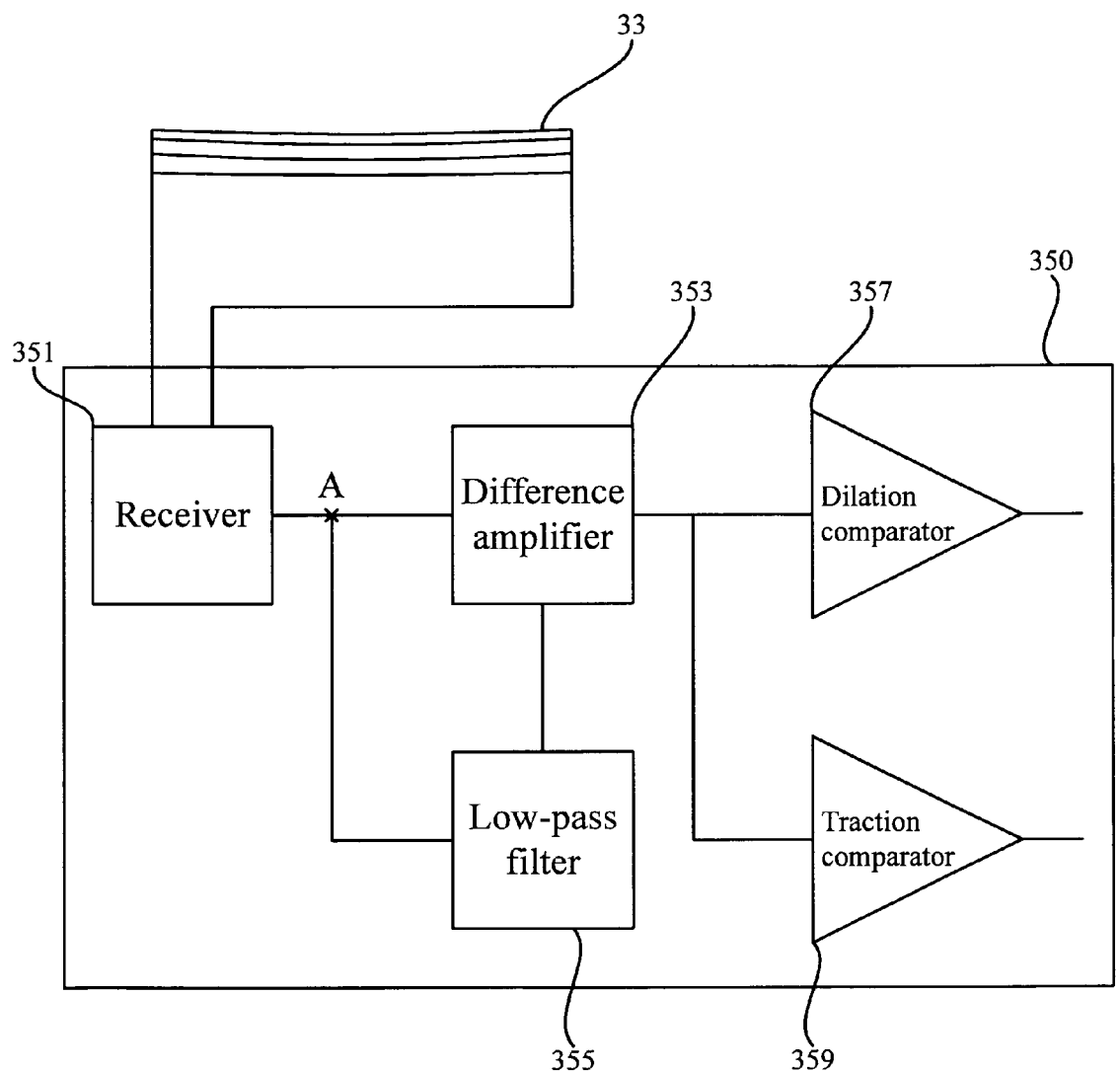
FIG. 5 shows a monitoring circuit of the monitoring module 35 of FIG. 4 for detecting change of voltage of the strain gauge of the invention.

Please further refer to FIG. 5, which shows a monitoring circuit of the monitoring module 35 of FIG. 4 for detecting change of voltage of the strain gauge of the invention. As shown in FIG. 5, the monitoring circuit 350 includes a receiver 351, a difference amplifier 353, a low-pass filter 355, a dilation comparator 357, and a traction comparator 359. It should be noted that the potential change at point A is relative change. For example, when the strain gauge 33 is elongated 1 cm for 5 sec., the potential at point A refers to a reference potential. When the strain gauge 33 is further extended, the potential at point A will be increased, and vice versa. That is to say, the reference potential is variable.

Furthermore, the receiver 351 can receive the signal generated by the strain gauge 33. The low-pass filter 355 can be combined with the difference amplifier 353 to provide a central voltage tracking and to dynamically amplify the signal to form an original signal. Moreover, the dilation comparator 357 can intercept the dilation signal during the user's inhaling from the original signal, whereas the traction comparator 359 can intercept the traction signal during the user's exhaling from the original signal.

Figure 6:
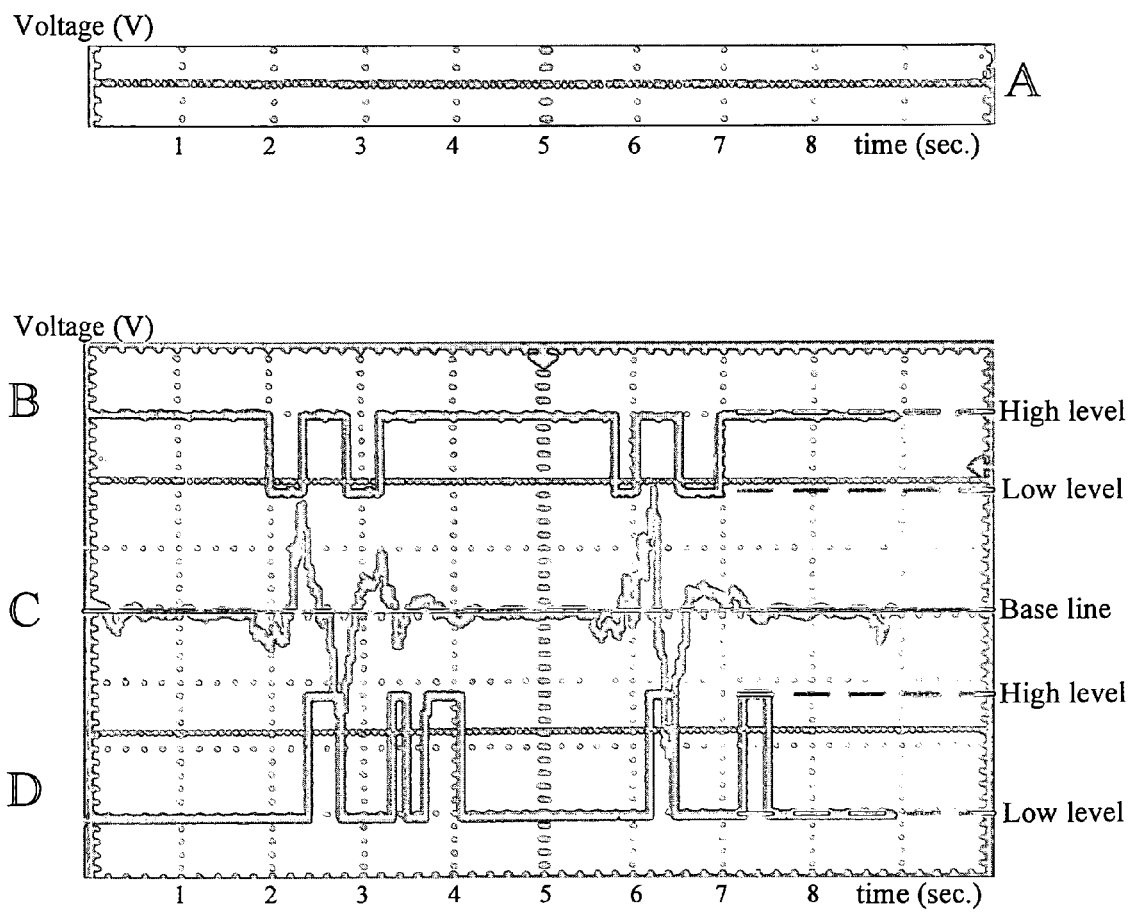
FIG. 6A illustrates the change of voltage when the garment shown in FIG. 4 is placed on a table without any outside force.
FIG. 6B illustrates the change of voltage of the garment of FIG. 4 worn by a user to monitor the respiration of the user.
FIG. 6C illustrates the change of voltage of the garment of FIG. 4 worn by a user to monitor the respiration of the user.
FIG. 6D illustrates the change of voltage of the garment of FIG. 4 worn by a user to monitor the respiration of the user.

In an example, a user wears a garment as shown in FIG. 4 to monitor his/her respiration. Moreover, the user receives the respiration monitoring under normal condition at room temperature. Please refer to FIG. 6A to FIG. 6D; FIG. 6A illustrates the change of voltage when the garment is placed on a table without any outside force, wherein the horizontal axis refers to time, and the vertical axis refers to the value of voltage; FIG. 6C illustrates the change of voltage due to respiration when the garment is worn by a user; FIG. 6B shows the change of voltage when the user is inhaling based on the original signal pattern of FIG. 6C after amplification and filtration by an amplifier. FIG. 6D shows the change of voltage when the user is exhaling based on the original signal pattern of FIG. 6C after amplification and filtration by an amplifier. It should be noted that the proportion of the change of voltage and the change of resistance is directly proportional.

In FIG. 6C, the curve located at the base line refers to that the strain gauge is static; the curve located over the base line refers to that the strain gauge is extended; and the curve located under the base line refers to that the strain gauge is relaxed. Furthermore, the positive slope of the curve refers to the strain gauge is from static to extended (inhaling); and the negative slope of the curve refers to the strain gauge is from extended to static (exhaling). Additionally, in FIG. 6B, the curve located at the low level refers to inhaling, whereas the curve located at the high level refers to exhaling or static. In FIG. 6D, the curve located at the high level refers to exhaling, whereas the curve located at the low level refers to inhaling or static. From FIG. 6B and FIG. 6D, it is clear that when the user is monitored under normal condition, because of the regular respiration, the periodic change of voltage/resistance is also regular. Please note that the principle of the increase or decrease of voltage/resistance should be further verify by scientific methods, but the verification is not in the aspect of the invention; thus, unnecessary details will not be given here. In addition, further comparison of FIG. 6A to FIG. 6D show that the strain gauge of the invention can clearly reflect the change of elongation/contraction and can perform with excellent sensitivity to actually reflect force received thereon.

Furthermore, when the strain gauge of the invention is acted on by an external force, the geometric property thereof will change and cause changes of the voltage/resistance thereof. As shown in FIG. 6A to FIG. 6D, when the voltage/resistance is changed, a pulse will be generated. In practice, the pulse can be used as a trigger signal for turning on/off an electrical device, such as a sound or light alarm, a lamp, a beeper and so on. Therefore, in practice, the strain gauge of the invention can be applied as a touch-type switch.

Obviously, the fabric-based strain gauge of the invention can be combined with a variety of fabrics, so as to fit to any kind of surface with excellent sensitivity and accuracy. More importantly, the fabric-based strain gauge of the invention can be developed to be a physical function monitoring apparatus comfortably worn by people to overcome the problems of the physical function monitoring apparatus of the prior art. Moreover, in addition to the field of medicine, the strain gauge of the invention can also be applied in many other fields.

What is claimed is:

1. A strain gauge, comprising:
   a fabric base weaved with a plurality of non-conductive yarns, and the fabric base thereon defining a sensing direction; and
   at least one conductive yarn, each of the conductive yarn being gimped with one of the non-conductive yarns by a textile process and woven through the fabric base along the sensing direction;
   wherein the at least one conductive yarn is capable of being applied by an electric power; when an external force acts on the fabric base, the geometrical property of the at least one conductive yarn alters so that a change of an electric property associated with the applied electric power is sensed to indicate an elongation or contraction of said strain gauge applied by the external force along the sensing direction.

2. The strain gauge of claim 1, wherein the electric property of the electric power is an impedance.

3. The strain gauge of claim 1, wherein the electric property of the electric power is a magnetic flux or an electric flux.

4. The strain gauge of claim 1, wherein at least one of the non-conductive yarns is elastic.

5. The strain gauge of claim 1, wherein the textile process is a weaving process or a knitting process.

6. The strain gauge of claim 1, wherein each of the at least one conductive yarn substantially contains textile fibers and metal fibers in an amount between 1 to 100 volume percentage.

7. The strain gauge of claim 6, wherein the metal fibers are formed of a stainless steel, a Ni—Cr alloy, or a Cu—Cr alloy.

8. The strain gauge of claim 7, wherein the diameter of each of the metal fibers is in a range from 1 µm to 30 µm.

9. The strain gauge of claim 1, wherein each of the at least one conductive yarn substantially contains textile fibers and metallic fibers in an amount between 1 to 100 volume percentage.

10. The strain gauge of claim 9, wherein the metallic fibers are formed from natural fibers, synthetic fibers, carbon fibers, or glass fibers, coated with Cu, Al, or Ag.

11. The strain gauge of claim 1, wherein each of the at least one conductive yarn is formed from an ultra-fine metal wire twisted with a plurality of textile fibers.

12. The strain gauge of claim 11, wherein the diameter of each of the ultra-fine metal wire is in a range from 10 µm to 80 µm.

13. The strain gauge of claim 12, wherein each of the ultra-fine metal wire is made of a stainless steel, a Ni—Cr alloy, or a Cu—Cr alloy.

14. The strain gauge of claim 12, wherein the strain gauge is capable of electrically connected to a monitoring circuit for detecting change of voltage of the strain gauge; wherein when the strain gauge is elongated or contracted and maintained at a length for a period, the potential of the strain gauge detected by the monitoring circuit will be assigned as a reference potential.

* * * * *